(12) United States Patent
Richter

(10) Patent No.: US 7,169,166 B2
(45) Date of Patent: *Jan. 30, 2007

(54) ACTIVE ARTERIAL EMBOLIZATION FILTER

(75) Inventor: Jacob Richter, Ramat Hasharon (IL)

(73) Assignee: Zuli Holdings, Ltd., Ramat Hasharon (IL)

( * ) Notice: Subject to any disclaimer, the term of this patent is extended or adjusted under 35 U.S.C. 154(b) by 367 days.

This patent is subject to a terminal disclaimer.

(21) Appl. No.: 10/304,433

(22) Filed: Nov. 26, 2002

(65) Prior Publication Data

US 2003/0212428 A1    Nov. 13, 2003

Related U.S. Application Data

(63) Continuation of application No. 09/583,363, filed on May 30, 2000, now Pat. No. 6,645,221.

(51) Int. Cl.
*A61M 29/00* (2006.01)
(52) U.S. Cl. ...................... 606/200; 600/434
(58) Field of Classification Search ................ 606/159, 606/113–114, 127, 193–195, 200; 604/22; 600/434, 585
See application file for complete search history.

(56) References Cited

U.S. PATENT DOCUMENTS 4,753,221 A    6/1988    Kensey et al.
4,794,928 A *  1/1989    Kletschka ............... 606/194
4,926,858 A *  5/1990    Gifford et al. .......... 606/159
5,490,859 A *  2/1996    Mische et al. .......... 606/159
5,895,399 A *  4/1999    Barbut et al. ........... 606/159
6,066,149 A *  5/2000    Samson et al. .......... 606/159
6,645,221 B1 * 11/2003   Richter .................... 606/200

FOREIGN PATENT DOCUMENTS

EP    0 976 417    2/2000
WO   WO99/23976   5/1999

* cited by examiner

*Primary Examiner*—Michael J. Hayes
*Assistant Examiner*—Victor X. Nguyen
(74) *Attorney, Agent, or Firm*—Kenyon & Kenyon LLP

(57) ABSTRACT

Apparatus for collecting emboli flowing in a lumen. A motor has a longitudinal bore, a friction area within the longitudinal bore, and a guide wire disposed within the longitudinal bore. The guide wire and friction area of the motor are sized and adapted to contact each other and impart friction between the friction area and the guide wire to permit the motor to rotate around the guide wire. A thrombus collecting gutter is attached to the motor. Paddles are attached to motor and are adapted to initiate a spiral blood flow when the motor rotates. The spiral blood flow causes thrombii in the blood to be deflected towards the internal wall of the lumen and be trapped in a thrombus collecting gutter which is positioned on the motor downstream of the paddles.

14 Claims, 6 Drawing Sheets

ACTIVE ARTERIAL EMBOLIZATION FILTER

RELATED PATENT APPLICATIONS

This application is a continuation of application Ser. No. 09/583,363 filed May 30, 2000, now U.S. Pat. No. 6,645,221

FIELD OF THE INVENTION

This invention relates generally to an arterial filter and method of filtering blood flowing within a lumen. More particularly, this invention relates to an active arterial embolization filter and method for actively collecting and removing emboli from a vessel being treated.

BACKGROUND OF THE INVENTION

The need for an arterial barrier or filter to prevent embolization of particles down-stream from the area being treated in the arterial system is well known, e.g., in percutaneous transluminal angioplasty (PTA). This need became especially clear and more urgent as the procedure of PTA (catheter based) treatment of the carotid arteries became more common. One of the major risks of stenting in the carotid arteries is the danger of emboli drifting downstream from the area being treated and causing transient ischemic attack(TIA). Several conventional devices have been utilized to try and prevent this danger to the patient. These devices are passive devices. One such conventional device is a balloon mounted on a catheter or on a guide wire that is inflated distal to the lesion being treated. Another such conventional device is an umbrella like filter placed distal to the lesion being treated. A major shortcoming of these conventional filters is that these conventional filters or barriers may greatly reduce, or even block, the downstream flow of blood from the treated artery to the brain, e.g., in the carotid artery. Another shortcoming of these devices is that they are passive.

OBJECTS AND SUMMARY OF THE INVENTION

It is an object of this invention to provide a device and method for actively removing emboli from an arterial bloodstream.

It is another object of this invention to provide an apparatus for disposing an active embolization filter device in the target area of a lumen comprising a motor having a proximal end and a distal end. The motor has a longitudinal bore and is provided with a motor friction area disposed within the longitudinal bore adapted to permit selective movement of the motor around the longitudinal axis of a guide wire disposed in the longitudinal bore. A guide wire having a longitudinal axis is disposed within the longitudinal bore and the guide wire and the longitudinal bore are sized and adapted to impart friction between the friction area of the motor and the guide wire in an amount sufficient to permit the motor to change position relative to the guide wire by rotating around the longitudinal axis of the guide wire when the motor is energized. A plurality of selectively deployable paddles is attached to the motor and are adapted for selective movement between a first collapsed or stored position when the motor is not energized to a second deployed position when the motor is energized. The paddles are further adapted to initiate a spiral blood flow in blood flowing through a lumen to deflect emboli towards the internal wall of the lumen when the paddles are in the second deployed position. In an especially preferred embodiment the paddles are adapted to move to the second or deployed position by centrifugal force imparted to them when the motor causes them to rotate around the longitudinal axis of a guide wire. A thrombus-collecting gutter having a closed bottom end and an open top end is attached to the motor and is adapted for selective movement between a first stored position when the motor is not energized to a second deployed position when the motor is energized. The gutter is disposed distal to the paddles with the open top end of the gutter disposed between the closed bottom end of the gutter and the paddles when the gutter is disposed in the deployed second position. The gutter is sized so that when it is in the second or deployed position the outer wall of the gutter is in contact with the inner wall of the lumen being treated. Means are provided for selectively energizing the motor and activating the motor friction area.

It is still another object of this invention to provide an apparatus for disposing an active embolization filter in the target area of a lumen comprising a cylindrically shaped housing having a proximal end and a distal end. The housing has a longitudinal bore adapted to permit selective movement of the housing along the longitudinal axis of a guide wire disposed in the longitudinal bore. A guide wire having a longitudinal axis is disposed within the longitudinal bore. A selectively deployable spiral blood flow initiator is attached to the housing and is adapted for selective movement between a first stored position and a second deployed position, and is adapted to initiate a spiral blood flow of blood flowing through a lumen and deflect emboli towards the internal wall of the lumen when the spiral blood flow initiator is in the second deployed position. In a preferred emodiment the spiral blood flow initiator is moved from the first stored position to the second deployed position by centrifugal force imparted by a rotating motor. A thrombus-collecting-gutter having a closed bottom end and an open top end and adapted for selective movement between a first stored position and a second deployed position is disposed on the guide wire distal to the spiral blood flow initiator. When the spiral blood flow initiator and the gutter are in the deployed second position the open top end of the gutter is disposed between the closed bottom end of the gutter and the spiral blood flow initiator. Means are provided for selectively moving the spiral blood flow initiator and the thrombus collecting gutter between the first stored position and the second deployed position.

DETAILED DESCRIPTION OF THE INVENTION

Miniature Oscillating Ceramic Motors (OCM) are well known in the art and are disclosed in U.S. Pat. No. 5,453,653 to Zumeris the specification of which is incorporated herein by reference. These motors can be made very small and in any shape and they operate by contacting a surface in an amount sufficient to generate sufficient friction to permit the motor to "crawl" along the contacted surface and change its position relative to the contacted surface when the motor is energized. These motors can be adequately insulated to act in aqueous environments. Their small size and low energy level requirements make them especially suitable for use inside living organisms.

Figure 1:
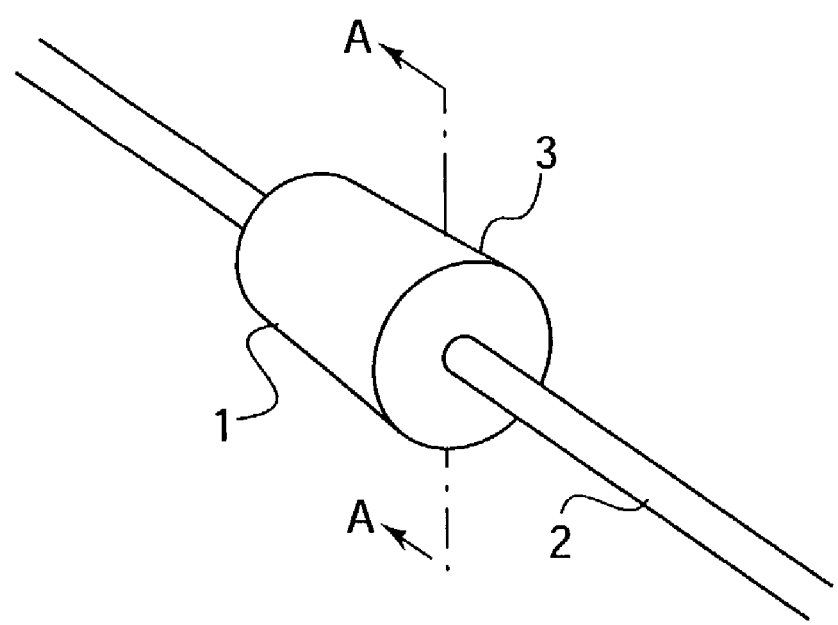
FIG. 1 shows a cylindrically shaped motor and a guide wire utilized in one embodiment of the invention to dispose an active embolization filter in the target area of a lumen.
Figure 2:
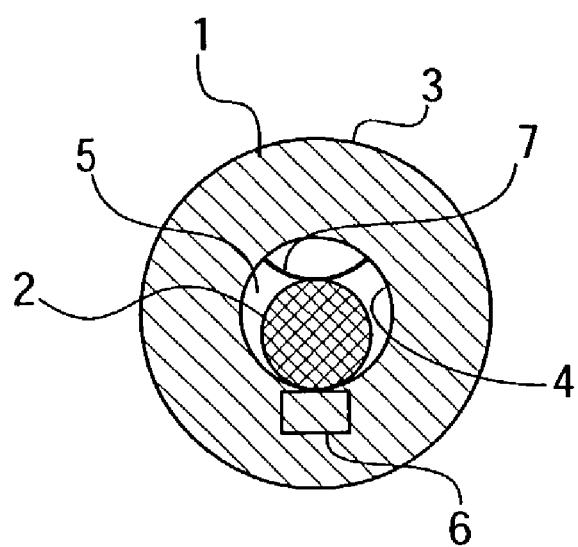
FIG. 2 is a cross-sectional end view of the embodiment of the invention shown in FIG. 1.

FIG. 1 is a lateral perspective of a portion of one embodiment of the invention and shows a cylindrical motor 1 having a longitudinal bore 5 there through. A guide wire 2 is disposed within the longitudinal bore 5. FIG. 2 is a cross-sectional end view taken on line A—A of FIG. 1 and shows the motor 1, preferably cylindrical, having an outer surface 3 and an inner surface 4 defining a longitudinal bore 5. The inner surface 4 defining the longitudinal bore 5 is provided with a friction area 6 adapted to engage the guide wire 2. The longitudinal bore 5 and the guide wire 2 are sized and adapted so that when the motor 1 is energized the friction area 6 engages the guide wire 2 and the motor 1 will rotate around the longitudinal axis 52 of the guide wire 2, thus, changing its position relative to the guide wire 2. In one embodiment, shown in FIG. 2, a biasing means, e.g., a leaf spring 7 is utilized to bias the guide wire 2 against the friction area 6 of the motor 1.

Figure 3:
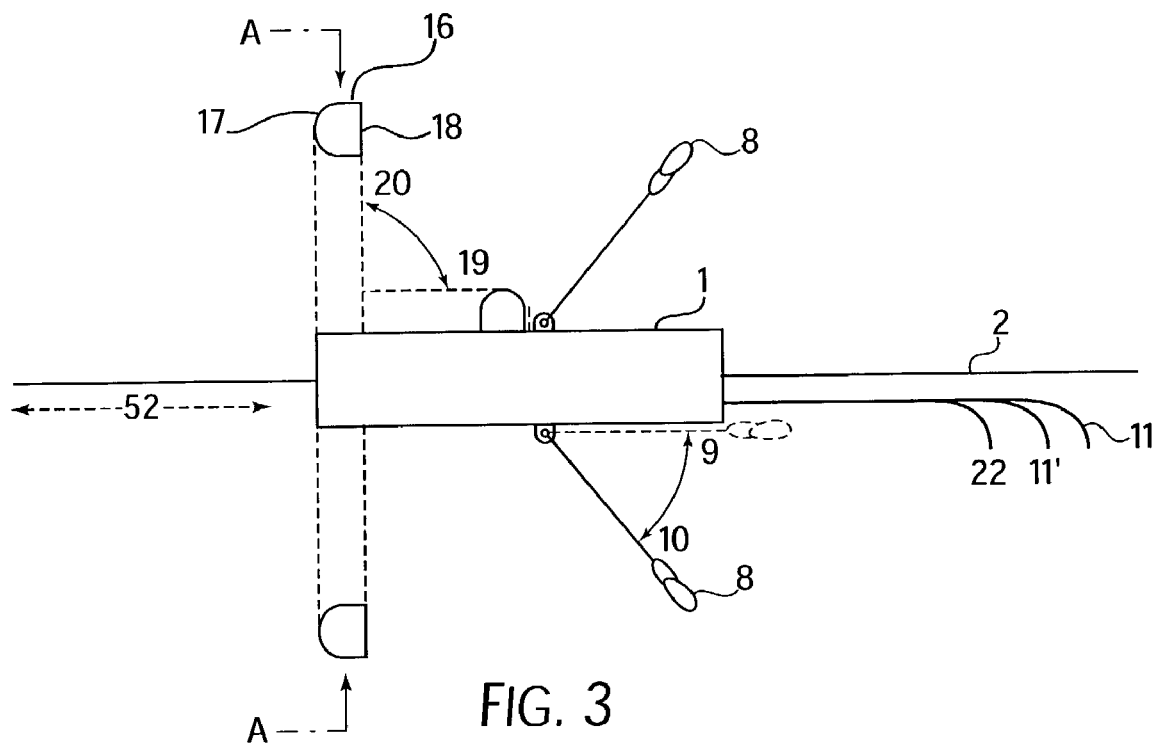
FIG. 3 is a side view of a preferred embodiment of the invention utilizing the motor and guide wire of FIGS. 1 and 2.
Figure 3A:
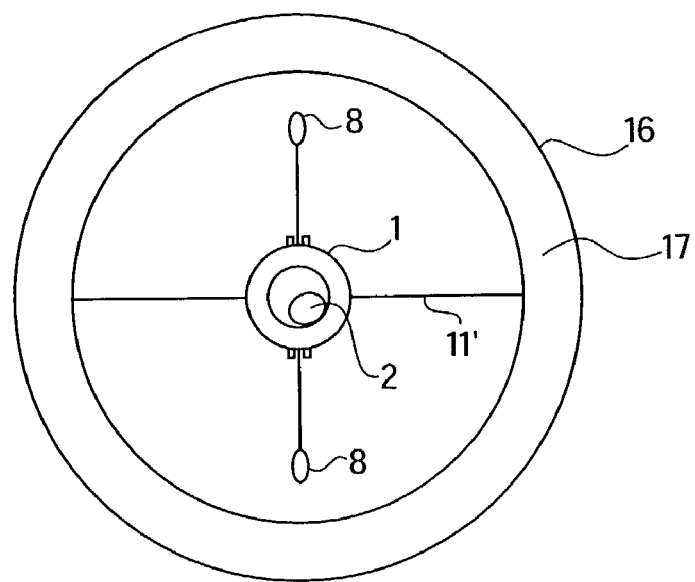
FIG. 3A is an end-view taken along line A—A of FIG. 3.
Figure 4:
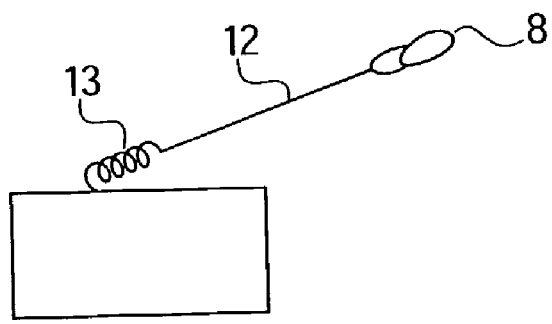
FIG. 4 shows one embodiment for attaching the paddles of an apparatus constructed in accordance with the invention.
Figure 5:
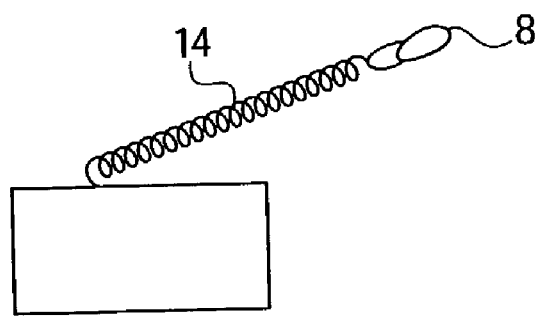
FIG. 5 shows an alternative embodiment for attaching the paddles of an apparatus constructed in accordance with the invention.
Figure 6:
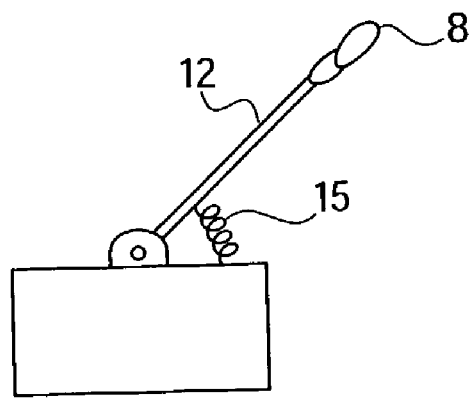
FIG. 6 shows an alternative embodiment for attaching the paddles of an apparatus constructed in accordance with the invention.
Figure 10A:
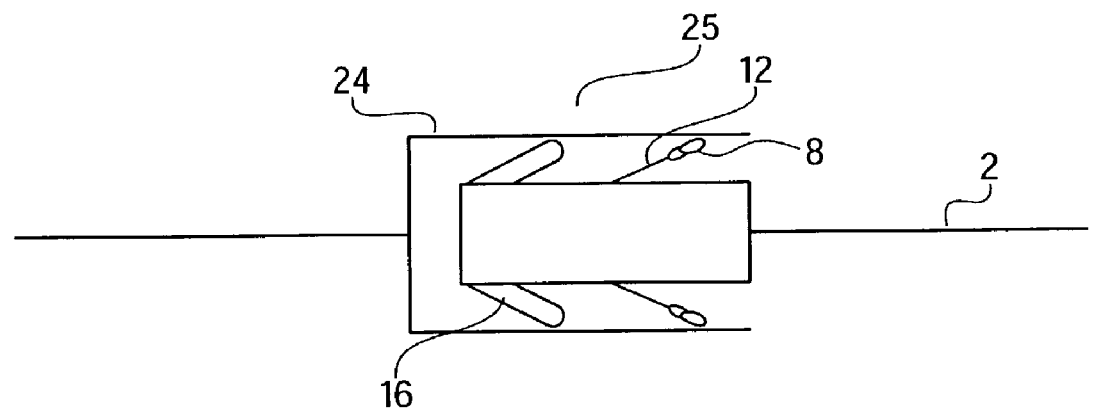
FIG. 10A shows an embodiment utilizing a sheath disposed in a first position in accordance with the invention.
Figure 10B:
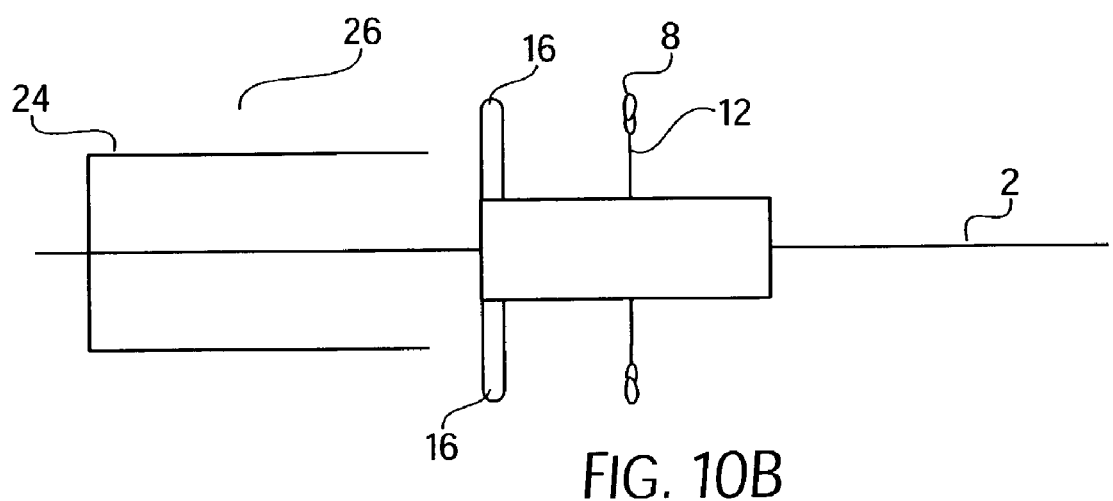
FIG. 10B shows the sheath of FIG. 10A disposed in a second position.

FIG. 3 is a side-view of a preferred embodiment of an invention that utilizes the motor and guide wire shown in FIGS. 1 and 2. FIG. 3A is an end-view of FIG. 3 taken along line A—A of FIG. 3. A plurality of selectively deployable paddles 8 is attached to the motor 1. The paddles 8 are adapted to be selectively movable between a first collapsed or stored position 9 when the motor 1 is not energized and a second or deployed position 10 when the motor 1 is energized. A wide variety of means well known to those skilled in the art as suitable for selectively moving the paddles 8 between the first stored position 9 and the second deployed position 10 may be utilized. In one embodiment, the paddles 8 may be made of an elastic material and may be moved from the first stored position 9 to the second deployed position 10 under their own elastic force after a locking wire 11 is released. After the treatment has been completed, the locking wire 11 may be activated to move the paddles 8 from the second deployed position 10 to the first stored position 9 to facilitate removal. In another embodiment, a sheath 24 selectively moveable along the longitudinal axis of the guidewire 2 is utilized to selectively move the paddles 8 between the first or stored position 9 to the second or deployed position 10. As shown in FIG. 10a, when the sheath 24 is in the first position 25 the paddles 8 are disposed in the first or stored position 9 and as shown in FIG. 10b, when the sheath 24 is disposed in the second position 26 the paddles 8 are free to move to the second or deployed position 10. The paddles 8 are returned to the first or stored position by moving the sheath 24 to the first position 25. In another preferred embodiment, the paddles 8 may be attached to arms 12 that are connected to the motor 1 via springs 13 as shown in FIG. 4. In yet another preferred embodiment, the paddles 8 are directly connected to the motor 1 via springs 14 as shown in FIG. 5. In an especially preferred embodiment, the paddles 8 are connected to arms 12 that are hingedly connected to the motor 1 and the arms 12 are provided with springs 15, as shown in FIG. 6, that normally keep the arms 12 and the paddles 8 in the first stored position 9. In an especially preferred embodiment, the paddles are sized and adapted so that when the motor 1 is energized and begins to rotate around the longitudinal axis of the guide wire 2, the centrifugal force of the rotating motor 1 causes the paddles 8 to move from the first stored position 9 to the second deployed position 10 and when the motor 1 stops rotating the absence of centrifugal force causes the paddles 8 to move to the first or stored position 9. The paddles 8 are sized and shaped so that as they rotate they initiate a spiral blood flood in the blood passing through the lumen. The swirling or cyclonic action caused by the rotating paddles 8 causes the emboli to flow towards the wall of the lumen and hug the lumen as the emboli travel with the blood flowing through the lumen. The emboli are then collected by a gutter positioned around the internal surface of the lumen. The gutter traps the emboli but allows blood to flow through the center of the lumen. When the treatment is finished, the motor is de-energized and the lack of centrifugal force allows the paddles to return to the first stored position.

A thrombus collecting gutter 16 having a closed bottom end 17 and an open top end 18 is disposed distal to the paddles 8. The thrombus collecting gutter 16 may be disposed on the motor or the guidewire and is adapted for selective movement between a first collapsed or stored position 19 and a second deployed position 20 as shown in FIG. 3. A wide variety of means well known to those skilled in the art as suitable for selectively moving the thrombus collecting gutter 16 between the first stored position and the second deployed position 20 may be utilized as previously discussed with respect to moving the paddles 8 from the first or stored position to the second or deployed position.

In one preferred embodiment, the thrombus collecting gutter 16 is made of an elastic material and may be moved from the-first stored position 19 to the second deployed position 20 under its own elastic force after a locking wire 11' is released. In another embodiment, the thrombus collecting gutter 16 is moved to the second or deployed position 20 by centrifugal force created by the rotating motor 1. In yet another embodiment a selectively movable sheath 24 is used to selectively move both the gutter and the paddles between a first stored position and a second deployed position as previously discussed and as shown in FIGS. 10A and 10B.

Figure 7:
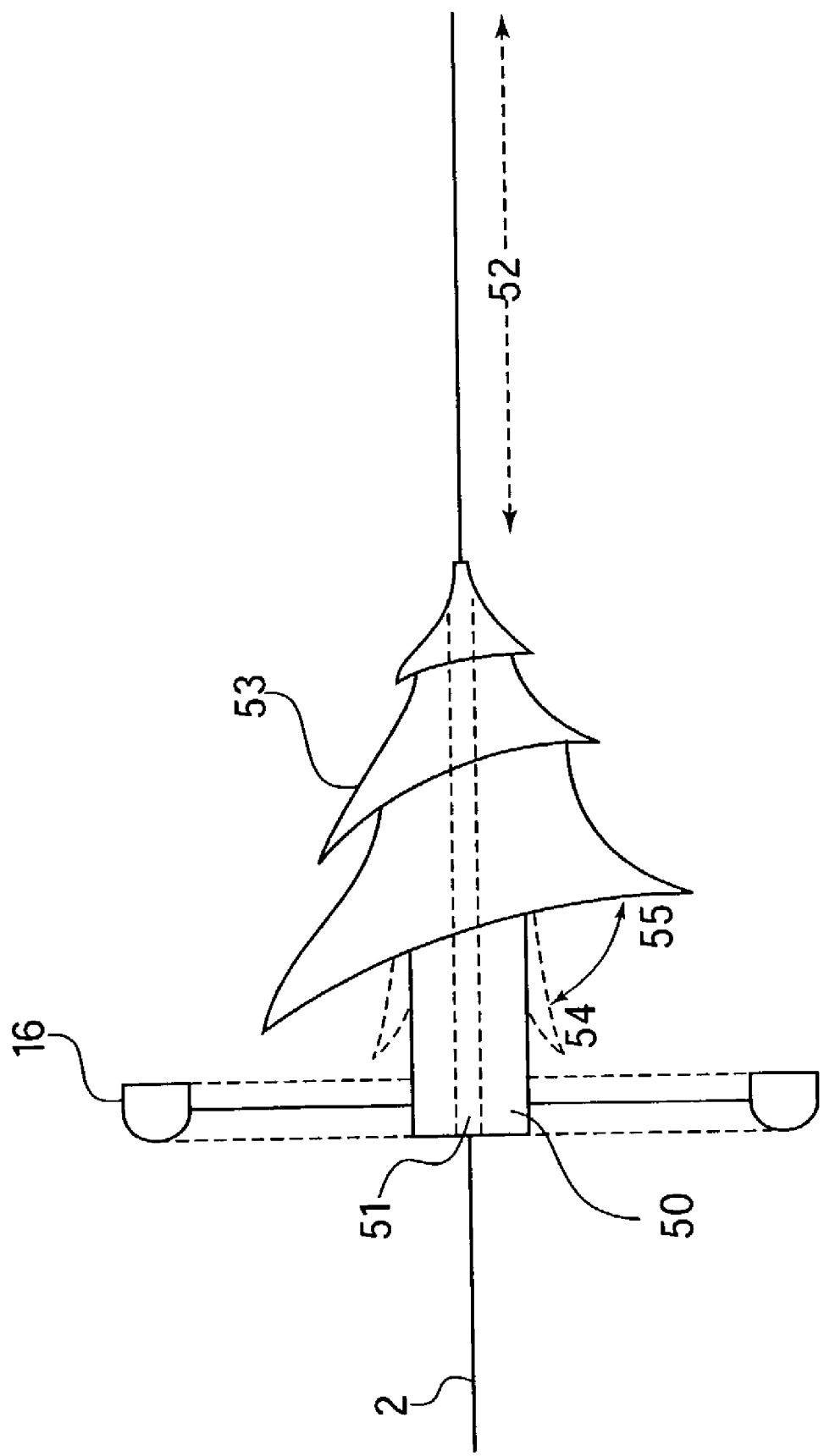
FIG. 7 shows a side view of another embodiment constructed in accordance with the invention that utilizes a spiral blood flow initiator.
Figure 8:
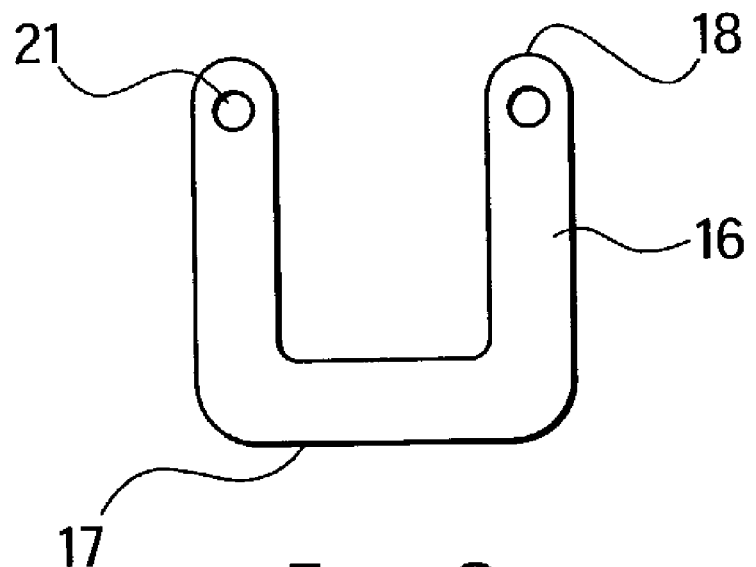
FIG. 8 shows one embodiment for selectively opening and closing the top end of thrombus collecting gutter constructed in accordance with the invention.
Figure 9:
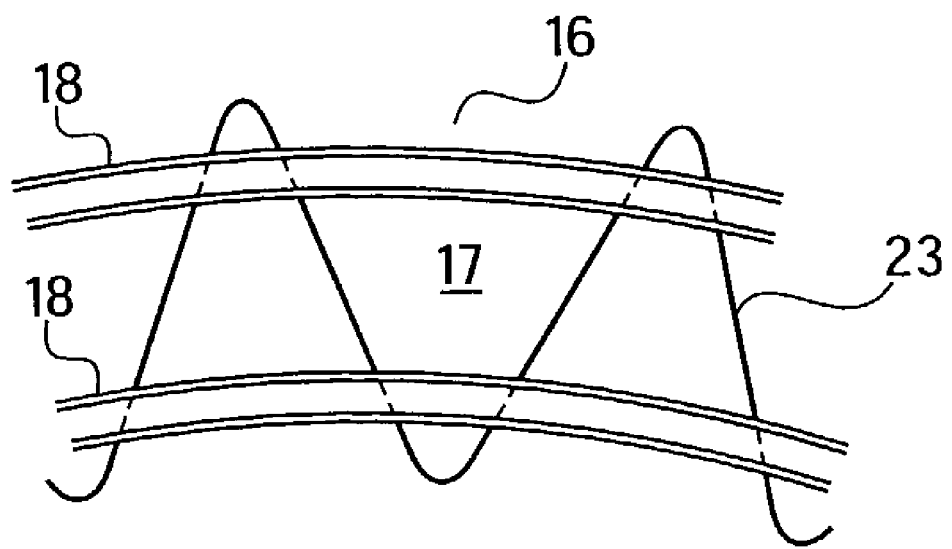
FIG. 9 shows an alternative embodiment for selectively opening and closing the top end of thrombus collecting gutter constructed in accordance with the invention.

When the thrombus collecting gutter 16 is in the first or stored position 19 it has a narrow streamlined configuration that permits it to be easily and safely disposed in and removed from the target area. In a preferred embodiment, the thrombus collecting gutter 16 has a substantially "U" shaped cross-sectional configuration, as shown in FIGS. 3, 7, and 8, when in the second deployed position 20 and an external diameter that is substantially equal to the internal diameter of the lumen being treated. When the thrombus collecting gutter 16 is disposed in the second deployed position 20 the open top end 18 is disposed between the bottom end 17 of the gutter 16 and the paddles 8, i.e., the open end 18 of the "U" faces the paddles 8 to permit thrombi diverted by the paddles to be trapped in the gutter 16. In an especially preferred embodiment, the top or open end 18 of the gutter 16 is adapted so that it may be selectively opened and closed and is provided with a means 21 for selectively opening and closing the top end of the gutter. The means 21 for selectively opening and closing the gutter may be selected from a wide variety of means well known to those skilled in the art as suitable for this purpose, however, in a preferred embodiment a trip wire 21 disposed along the periphery of the top end of the gutter is utilized. Alternatively, the trip wire 21 may be embedded within the top end 18 of the gutter as shown in FIG. 8. The trip wire 21 is preferably connected to an activation means such as a lever or a wire 22 for selectively opening and closing the top end 18 of the gutter 16. In an especially preferred embodiment the top end 18 of the gutter 16 is provided with a wire or filament 23 that traverses the open end of the gutter for selectively opening and closing the open top end 18 of the gutter 16 as shown in FIG. 9. When the wire or filament 23 is pulled or tugged by an activation means such as a lever or wire 22, the wire or filament 23 causes the open end 18 of the gutter 16 to close in the same way that pulling on a sewing thread connecting two pieces of cloth causes the two pieces of cloth to move closer to each other.

In operation of a preferred embodiment, the apparatus is constructed, mounted on a guide wire and is manually advanced to the target area which is downstream from the area that is being treated. The motor is then energized to activate the motor friction area which causes the motor to rotate around the longitudinal axis of the guide wire. The centrifugal force created by the rotating motor causes the gutter and the paddles to move from the first stored position to the second deployed position with the open end of the gutter facing the paddles. The rotating paddles create a swirling action or spiral blood flow in the blood like a propeller rotating in water which causes emboli in the blood to flow toward and be propelled against the internal wall of the lumen. The emboli hug the internal wall of the lumen as the blood forces them downstream and into the open end of the gutter. When the treatment is complete the motor is de-energized which causes the motor to stop rotating and causes the paddles and the gutter to return to the first collapsed or stored position. In some applications it may be desirable to utilize a gutter whose open top end may be selectively opened and closed. In this embodiment the open top end of the gutter may be closed before it is moved from the second deployed position to the first stored position to help retain the trapped emboli and reduce the likelihood that they will spill out of the gutter into the bloodstream as the apparatus is removed from the lumen. The apparatus may then be manually removed by pulling on the guide wire.

FIG. 7 shows another preferred embodiment of the invention and shows a motor 50, preferably cylindrically shaped, having a longitudinal bore 51 sized and adapted to permit selective movement of the motor 50 around the longitudinal axis 52 of a guide wire 2 disposed within the longitudinal bore 51. A spiral blood flow initiator 53 is attached to the motor 50 and is adapted to permit the spiral blood flow initiator 53 to be selectively moved between a first collapsed or stored position 54 to a second deployed position 55. The spiral blood flow initiator 53 is also sized and adapted to initiate a spiral or cyclonic blood flow sufficient to deflect any emboli in the flowing blood towards the internal wall of the lumen in which the blood is flowing. A thrombus collecting gutter 16, previously discussed, is disposed either on the motor 50 or the guidewire 2 distal to the spiral blood flow initiator 53 with the open top end 18 of the gutter 16 disposed between the closed bottom end 17 of the gutter 16 and the spiral blood flow initiator 53 when the gutter 16 and the spiral blood flow initiator 53 are in the deployed second position 55. Means are provided for selectively moving the spiral blood flow initiator and the gutter between the first stored position and the second deployed position as previously discussed. In a preferred embodiment, a rotating motor 50 is utilized to create centrifugal force to both deploy and retract both the gutter 16 and the spiral blood flow initiator 53 as previously discussed.

In operation, the device is advanced to the target area and the spiral blood flow initiator 53 and the gutter 16 are moved from the first position 19 and 54 to the second or deployed position 20 and 55. As the blood flowing in the lumen strikes the spiral blood flow initiator 53, the spiral blood flow initiator 53 initiates a spiral or cyclonic blood flow which deflects or propels emboli against the internal wall of the lumen so that they can be trapped in the gutter 16 as previously discussed. The gutter 16 and the spiral blood flow initiator 53 are then returned to the first collapsed or stored position 19 and 54 and the apparatus is withdrawn from the target area. The gutter may be adapted to be selectively opened and closed as previously discussed.

While the invention has been described with respect to a limited number of embodiments, it will be appreciated that many variations, modifications, and other applications of the invention may be made.

What is claimed is:

1. An apparatus for collecting debris flowing in a lumen, comprising:
    a. a blood flow initiator adapted to initiate a swirling flow of blood through a lumen to deflect debris towards the internal wall of the lumen including:
        i. a guide wire,
        ii. a plurality of paddles supported for rotation about the guide wire, and
        iii. a driving member coupled to said paddles to rotate said paddles about said guide wire; and
    b. an annular debris collecting receptacle disposed at or near the inner wall of the lumen distal to the blood flow initiator.

2. An apparatus according to claim 1 wherein said flow is a spiral flow.

3. An apparatus according to claim 1 wherein the receptacle is adapted for selective movement between a first stored position and a second deployed position.

4. An apparatus according to claim 3 wherein the blood flow initiator adapted for selective movement between a first stored position and a second deployed position.

5. An apparatus according to claim 1 wherein the paddles are adapted for selective movement between a first stored position and a second deployed position.

6. An apparatus according to claim 1 and further including:
   a. a housing having a proximal end and a distal end, the housing having a longitudinal bore sized and adapted to permit selective movement of the housing along a longitudinal axis of said guide wire, said paddles mounted to said housing, said driving member adapted to rotate said housing.

7. An apparatus according to claim 6, wherein said driving member comprises a motor.

8. An apparatus for collecting debris flowing in a lumen, comprising:
   a. means to initiate a swirling flow of blood through a lumen to deflect debris towards the internal wall of the lumen including:
      i. a guide wire,
      ii. a plurality of paddles supported for rotation about the guide wire, and
      iii. means to rotate said paddles about said guide wire; and
   a. means for collecting debris disposed at or near the inner wall of the lumen distal to the means to initiate.

9. An apparatus according to claim 8 wherein said flow is a spiral flow.

10. An apparatus according to claim 8 wherein said means for collecting debris is adapted for selective movement between a first stored position and a second deployed position.

11. An apparatus according to claim 10 wherein said means to initiate are adapted for selective movement between a first stored position and a second deployed position.

12. An apparatus according to claim 8 wherein said means to initiate are adapted for selective movement between a first stored position and a second deployed position.

13. An apparatus according to claim 8 and further including:
   a. a housing having a proximal end and a distal end, the housing having a longitudinal bore sized and adapted to permit selective movement of the housing along a longitudinal axis of said guide wire, and wherein:
   b. said means to initiate are mounted to said housing, and
   c. said means to rotate are adapted to rotate said housing.

14. An apparatus according to claim 13, wherein said means to rotate comprises a motor.

* * * * *